(12) United States Patent
Waterman et al.

(10) Patent No.: US 11,458,036 B2
(45) Date of Patent: Oct. 4, 2022

(54) ORAL APPLIANCE APPARATUS AND METHOD OF OPERATION THEREOF

(71) Applicants: Rick T. Waterman, Tiburon, CA (US); Jack O. Mills, Livermore, CA (US)

(72) Inventors: Rick T. Waterman, Tiburon, CA (US); Jack O. Mills, Livermore, CA (US)

(73) Assignee: Rick T. Waterman, Tiburon, CA (US)

( * ) Notice: Subject to any disclaimer, the term of this patent is extended or adjusted under 35 U.S.C. 154(b) by 16 days.

(21) Appl. No.: 17/241,101

(22) Filed: Apr. 27, 2021

(65) Prior Publication Data

US 2021/0330488 A1 Oct. 28, 2021

Related U.S. Application Data

(60) Provisional application No. 62/704,230, filed on Apr. 28, 2020.

(51) Int. Cl.
*A61F 5/56* (2006.01)
(52) U.S. Cl.
CPC .................................. *A61F 5/566* (2013.01)
(58) Field of Classification Search
CPC ...... A61F 5/56; A61F 2005/563; A61F 5/566; A63B 71/085; A63B 71/086; A63B 71/088; A61M 16/0616; A61M 16/0666; A61M 16/0672; A61M 2016/0661; A61M 16/0694
See application file for complete search history.

(56) References Cited

U.S. PATENT DOCUMENTS

| | | | | |
|---|---|---|---|---|
| 2,705,006 A | * | 3/1955 | Cettel | A61F 5/566 128/857 |
| 5,467,783 A | * | 11/1995 | Meade | A61F 5/566 128/859 |
| 5,592,951 A | * | 1/1997 | Castagnaro | A61F 5/566 128/862 |
| 5,983,892 A | * | 11/1999 | Thornton | A62B 9/06 128/206.29 |
| 6,053,168 A | * | 4/2000 | Sue | A61F 5/566 128/859 |
| 6,231,337 B1 | * | 5/2001 | Boyd | A61C 7/08 433/6 |
| 6,412,489 B1 | * | 7/2002 | Sue | A61F 5/566 128/859 |
| 6,491,037 B1 | * | 12/2002 | Mortenson | A61B 5/01 128/859 |
| 2016/0193074 A1 | * | 7/2016 | Thynne, Jr. | A61F 5/56 128/848 |
| 2019/0269995 A1 | * | 9/2019 | Effert | A63B 71/085 |
| 2019/0282345 A1 | * | 9/2019 | Friebauer | A61C 13/0025 |
| 2021/0162156 A1 | * | 6/2021 | Farrell | A61C 7/36 |

* cited by examiner

*Primary Examiner* — Tarla R Patel
(74) *Attorney, Agent, or Firm* — Xhavin Sinha (57) ABSTRACT

A device for treating sleep disorders such as snoring and sleep apnea comprising an upper portion, and a lower portion; wherein a first bottom surface of the upper portion, is joined to a second top surface of the lower portion using a sealant. A method of treating sleep disorders such as snoring and sleep apnea includes using an oral appliance, and a positive airway pressure machine for assisting a user to breathe through the nose.

16 Claims, 7 Drawing Sheets

ORAL APPLIANCE APPARATUS AND METHOD OF OPERATION THEREOF

TECHNICAL FIELD

An embodiment of the present invention relates generally to a dental appliance. In particular, to the construction, and use of the dental appliance to help people to breathe through the nose and help improve sleep without the need to adjust the jaw.

BACKGROUND ART

Some people throughout the world suffer from not being able to comfortably sleep a consistent period of time. Sleep cycles include Stages 1 through 4 and Rapid Eye Moment (REM) sleep. Some of the reasons for not being able to get a full sleep cycle include sleep apnea, snoring, or other related sleep breathing issues.

A reason for the breathing issues is that the muscles in the throat relax which causes the tissues to collapse into the airway. The air cannot move freely as a result and can cause vibrations in the airways leading to snoring and to other breathing issues.

Solutions have focused on positioning of the jaw which can prevent tissue collapse and thus keep the air moving through the airway.

Research and development in the existing technologies can take a myriad of different directions such as the development of mandibular adjustment devices. These mandibular adjustment devices can be uncomfortable, and further cause unnatural positions in order to try and solve breathing problems related to sleep.

Other solutions have focused on inefficient methods to prevent breathing through the mouth such as tape or chin straps which do not effectively prevent mouth breathing comfortably, or for a prolonged period. Solutions involving tape can leave adhesive in sensitive areas that over time causes irritation and accumulation on the face. Adhesives can also dissolve due to drooling resulting in failure of taping. Thus, a need still remains for a comfortable and natural solution.

Solutions to these problems have been long sought but prior developments have not taught or suggested any solutions and, thus, solutions to these problems have long eluded those skilled in the art.

DISCLOSURE OF INVENTION

An embodiment of the present invention provides an apparatus, comprising: a single piece oral appliance configured to prevent breath from escaping through the mouth and forcing breath through the nose for assisting in sleeping for a user.

An embodiment of the present invention provides an apparatus, comprising: a single piece oral appliance configured to greatly diminish breath from escaping through the mouth and forcing breath through the nose for assisting in sleeping for a user.

An embodiment of the present invention provides an apparatus, comprising: an upper portion, comprising a front side, a rear side, a top side, and a bottom side; a lower portion, comprising a front side, a rear side, a top side, and a bottom side; a sealing material where the sealing material joins the upper portion, and the lower portion together along the bottom side of the upper portion, and the top side of the lower portion; configured to prevent breath from escaping through the mouth and forcing breath through the nose for assisting in sleeping for a user.

An embodiment of the present invention provides an apparatus, comprising: an upper portion, comprising a front side, a rear side, a top side, and a bottom side; a lower portion, comprising a front side, a rear side, a top side, and a bottom side; a sealing material where the sealing material joins the upper portion, and the lower portion together along the bottom side of the upper portion, and the top side of the lower portion; configured to greatly diminish breath from escaping through the mouth and forcing breath through the nose for assisting in sleeping for a user.

An embodiment of the present invention provides an apparatus, comprising: an upper portion, and a lower portion that is constructed to fit into an appliance location of a user wherein the one-piece appliance is configured to prevent air flow from occurring from the mouth region or a user.

An embodiment of the present invention provides a method of operation of an apparatus, comprising: placing an oral appliance in a mouth of a user; preventing any breath through the mouth of the user; and forcing breathing through a nose of the user.

An embodiment of the present invention provides a method of operation of an apparatus, comprising: placing an oral appliance in a mouth of a user; placing a mask on the user; using a positive airway pressure (CPAP/BI-PAP) system with the oral appliance, and the mask; and breathing through a nose of the user.

An embodiment of the present invention provides a method of manufacturing of an oral appliance comprising: receiving a material; placing the material in a hot environment; removing the material from the hot environment; molding the material into an oral appliance.

An embodiment of the present invention provides a method of manufacturing of an oral appliance comprising: receiving a material, an upper form, and a lower form; using a forming machine, the material, the upper form, and the lower form to make an upper portion, and a lower portion; receiving a sealant; configuring the upper portion, the lower portion, and the sealant to make an oral appliance.

An embodiment of the present invention provides a method of manufacturing of a one-piece appliance comprising: receiving a material, an upper form, and a lower form; using a forming machine, the material, the upper form, and the lower form to make an upper portion, and a lower portion; receiving a sealant; configuring the upper portion, the lower portion, and the sealant to make an oral appliance.

Certain embodiments of the invention have other steps or elements in addition to or in place of those mentioned above. The steps or elements will become apparent to those skilled in the art from a reading of the following detailed description when taken with reference to the accompanying drawings.

BEST MODE FOR CARRYING OUT THE INVENTION

Embodiments provide the oral appliance, the CPAP/BI-PAP system, or a combination thereof can increase sleep comfort without the need for uncomfortable mandible adjustments.

Embodiments provide the oral appliance, the CPAP/BI-PAP system, or a combination thereof can provide an efficient method for breathing through the nose, and prevent breathing through the mouth.

Embodiments provide the oral appliance, helps to increase the effectiveness of the CPAP/BI-PAP system to treat sleep disorders such as sleep apnea, reduce snoring or a combination thereof.

The following embodiments are described in sufficient detail to enable those skilled in the art to make and use the invention. It is to be understood that other embodiments would be evident based on the present disclosure, and that system, process, or mechanical changes may be made without departing from the scope of an embodiment of the present invention.

In the following description, numerous specific details are given to provide a thorough understanding of the invention. However, it will be apparent that the invention may be practiced without these specific details. In order to avoid obscuring an embodiment of the present invention, system configurations, and process steps are not disclosed in detail.

The drawings showing embodiments of the system are semi-diagrammatic, and not to scale and, particularly, some of the dimensions are for the clarity of presentation and are shown exaggerated in the drawing figures. Similarly, although the views in the drawings for ease of description generally show similar orientations, this depiction in the figures is arbitrary for the most part. Generally, the invention can be operated in any orientation. The embodiments have been numbered first embodiment, second embodiment, etc. as a matter of descriptive convenience and are not intended to have any other significance or provide limitations for an embodiment of the present invention. The terms first, second, etc. can be used throughout as part of element names and are used as a matter of descriptive convenience and are not intended to have any other significance or provide limitations for an embodiment.

Figure 1:
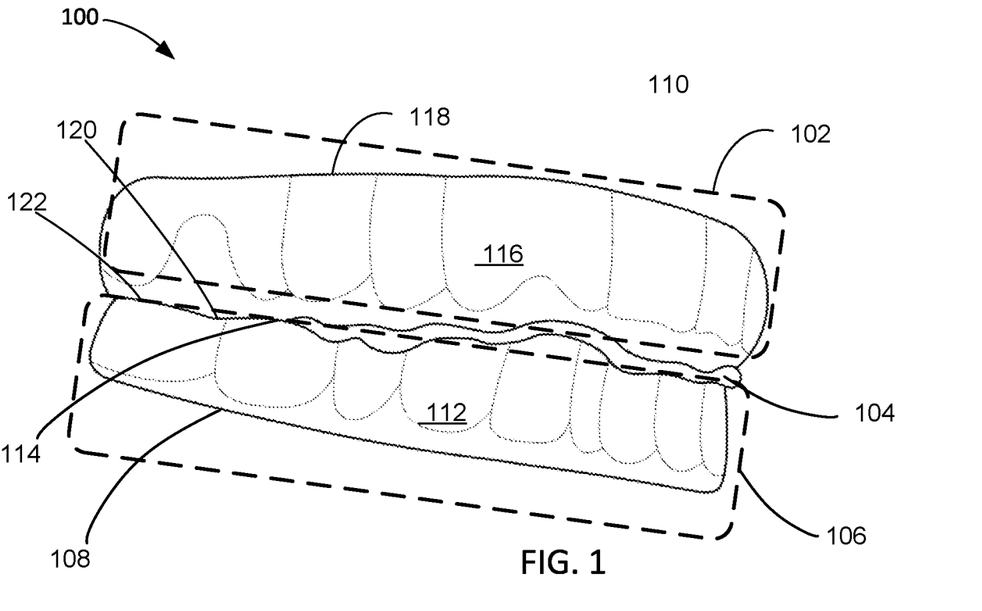
FIG. 1 is an example of an illustration of the front of an embodiment 100 of the present invention.

Referring now to FIG. 1, therein is shown an example of an illustration of the front of an embodiment 100 of the present invention. An oral appliance 110 includes an upper portion 102, a sealant 104, and a lower portion 106. The upper portion 102 is joined to the lower portion along a second top side 114 of the lower portion, and a first bottom side 120 of the upper portion, using the sealant 104. The oral appliance 110 is configured to prevent airflow through the device when in use.

Figure 2:
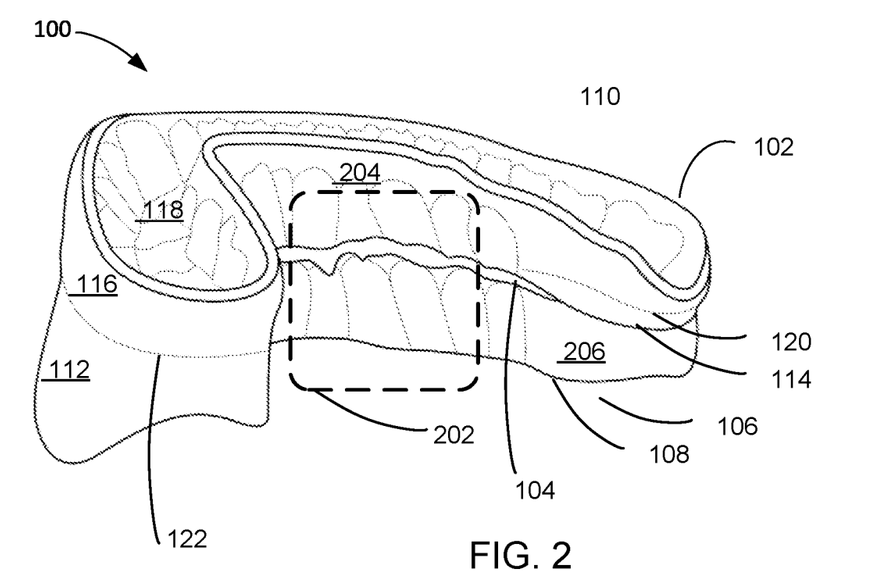
FIG. 2 is an example of an isometric illustration of the rear of an embodiment 100 of the present invention.

The upper portion 102 can include a first top side 118, a first front side 116, a first bottom side 120, and a first rear side 204 of FIG. 2. The lower portion 106 can include a second top side 114, a second front side 112, a second bottom side 108, and a second rear side 206 of FIG. 2. The first top side 118, the front side 116, the first bottom side 120, and the first rear side 204 of FIG. 2 can describe the upper portion with respect to its orientation relative to its position of placement within the mouth area 434 of FIG. 4 of the user 410 of FIG. 4. The first front side 116, can be described as the side where the majority of the side faces opposite to the first rear side 204 of FIG. 2. There are parts of the first front side 116 which wrap and connect to the first rear side 204 and this is depicted in FIG. 2. The first rear side 204 of FIG. 2 faces the inside of the mouth area 434 of FIG. 4 of the user 410 of FIG. 4. The first top side 118 can be described as containing the upper dental arch 438 of the upper jaw 418 of FIG. 4 of FIG. 4 of the user 410 in FIG. 4. The first bottom side 120 can be described as the side adjacent to the upper dental arch 438 of FIG. 4 of the user 410 of FIG. 4 and opposite the first top side 118.

Figure 4:
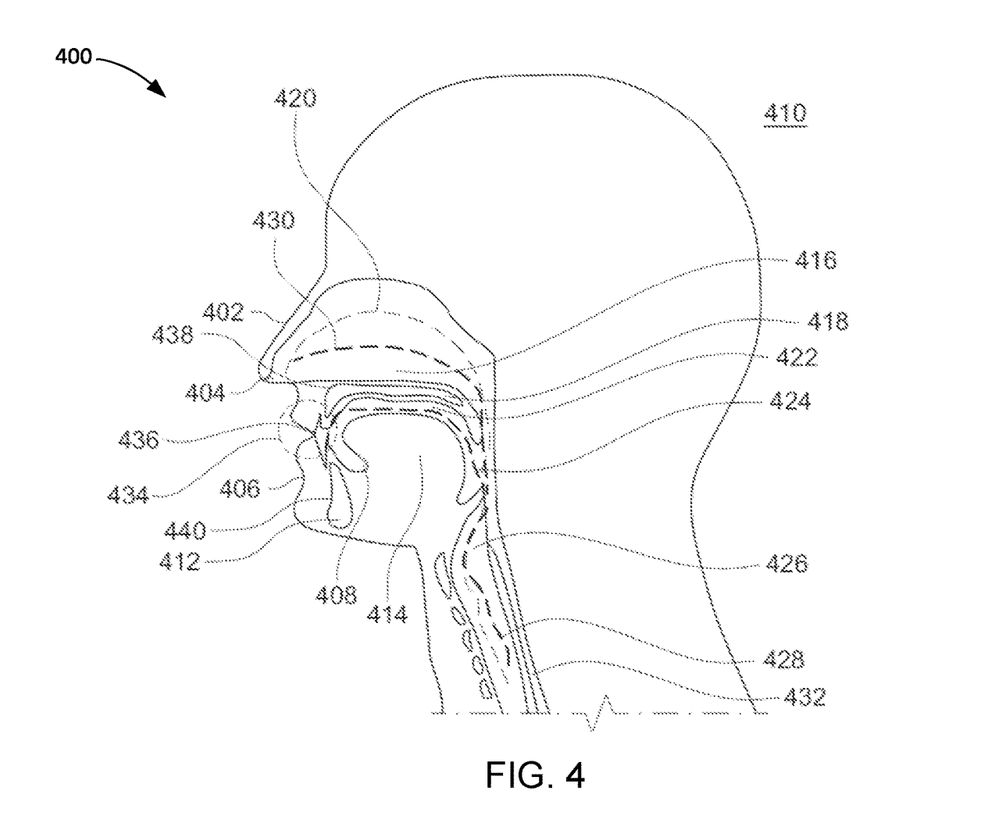
FIG. 4 is an example of a section detail view of one embodiment 400 of the present disclosure.

The second top side 114, the second front side 112, the second bottom side 108, and the second rear side 206 of FIG. 2 describe the lower portion with respect to its orientation relative to its position of placement within the mouth area 434 of FIG. 4 of the user 410 of FIG. 4. The second front side 112, can be described as facing opposite the second rear side 206 of FIG. 2. There are parts of the second front side 112 which wrap and connect to the second rear side 206 and this is depicted in FIG. 2. The second rear side 206 of FIG. 2 faces the inside of the mouth area 434 of FIG. 4 of the user 410 of FIG. 4. The second top side 114 can be described as adjacent to the lower dental arch 440 of FIG. 4 of the user 410 in FIG. 4. The second bottom side 108 can be described as the side containing the lower dental arch 440 of FIG. 4 of the user 410 of FIG. 4 and opposite the second top side 114.

The upper portion 102, can be constructed to fit the upper dental arch 438 in FIG. 4 for the user 410 in FIG. 4. The lower portion 106, can be constructed to fit the lower dental arch 440 in FIG. 4 for the user 410 in FIG. 4.

For example, the upper portion 102, and the lower portion 106 can each be constructed by material that is non-toxic, hypoallergenic, or a combination thereof. For example, the material can include acrylic, or heat forming plastic or, a combination thereof. In another example, each component can be the constructed of a same material, a different material, or a combination thereof.

In another example, the construction can include molding, 3-D printing, or a combination thereof.

The upper portion 102, and the lower portion 106 can be joined together using a sealant 104. The upper portion 102 can include the first bottom side 120, that can be joined to the second top side 114 of the lower portion 106. The joining material can be the sealant 104.

The sealant 104 is an adhesive material which can be capable of joining the upper portion 102 and the lower portion 106 together to form a junction 122. The junction 122 can be the location where the first bottom side 120 of the upper portion 106 meets the sealant 104, and the second top side 114 of the lower portion. This junction is 122 is airtight, and once the sealant 104 is set, the upper portion 102, and the lower portion 106 can be fixed in place essentially making the upper portion 102, and the lower portion 104 function as one unit. Airflow can be impeded from exiting the mouth area 434 in FIG. 4 from the user 410 in FIG. 4.

The sealant 104, for example, can be placed along the entire surface of the second top side 114 of the lower portion, the entire surface of the first bottom side 120 of the upper portion, or a combination thereof.

In this configuration, the sealant 104 can function to fill in any gaps along the first bottom side 120 of the upper portion 106, the second top side 114 of the lower portion, or a combination thereof. The sealant 104 can also function to ensure that no air is able to pass out of the mouth area 434 of FIG. 4 from the user 410 in FIG. 4. The sealant also can function to join the upper portion 102, and the lower portion 106 together such that they are not able to come apart.

In another embodiment, the controlled placement of the sealant 104 along the first bottom side 120 of the upper portion 106, the second top side 114 of the lower portion, or a combination thereof can control that amount of air flow through the oral appliance 110. For example, if the sealant 104 is placed at regular intervals, along each surface, on joining the surfaces, and drying of the sealant, the oral appliance 110 can have small gaps created to permit minimal airflow through the oral appliance.

In another embodiment, the sealant 104 placed along the entire first bottom side 120 of the upper portion 106, the entire second top side 114 of the lower portion, or a combination thereof can prevent airflow through the oral appliance.

The material for the sealant can include nontoxic, hypoallergic adhesives, acrylic, thermo plastics, silicon, rubber, other comparable materials, or a combination thereof. The sealant can be for example, the same material used to construct the upper portion 102, the lower portion 104, or a combination thereof.

For illustrative purposes, the upper portion 102, the lower portion 106, and the sealant 104 can be configured into a single piece oral appliance 110, where the upper portion 102, and the lower portion 104 can be joined using the sealant 104.

The upper portion 102, and the lower portion 106 can be sized to ensure that a complete seal can be formed between the oral appliance 110 and the mouth area 434 of FIG. 4 when placed in the appliance location 436 of FIG. 4 of the user 410 of FIG. 4. A first seal can be formed along the upper jaw 418 provided the upper portion 102 can cover the upper dental arch 438 of FIG. 4 and the portion of the upper gumline. Similarly, a second seal can be formed along the lower jaw 412 provided the lower portion 106 can cover the lower dental arch 440 of FIG. 4 and the portion of the lower gumline. The first seal, and the second seal together can form a complete seal. The complete seal thereby prevents air from escaping through the mouth area 434.

A complete seal is when the sealant 104 completely joins the first bottom surface 120 of the upper portion 102, to the second top surface 114 of the lower portion 106 such that there is no space for air to flow across the first bottom surface 120 of the upper portion 102, and the second top surface 114 of the lower portion 106.

The upper portion 102 dimensions and lower portion 106 dimensions can be configured as such to; mold to the upper dental arch 438 of FIG. 4 of the user 410 of FIG. 4, and the lower dental arch 440 of FIG. 4 of the user 410 of FIG. 4; ensure a complete seal is formed for the user 410 of FIG. 4 or; a combination thereof. For example, a complete seal can include the situation where there in minimal air that is expelled through the mouth area 434 in the form of a leak where there is an improper seal.

An improper seal can include a defect where the complete seal was not made using the sealant 104. An improper seal can also include where the device does not form a seal with the mouth thereby allowing air to leak in, air to leak out or a combination thereof.

Referring now to FIG. 2, therein is shown an example of an isometric illustration of the rear of an embodiment 100 of the present invention. FIG. 2 provides a view of the oral appliance 110 depicting the upper portion 102, the lower portion 106, and the sealant 104.

The upper portion 102 depicts the first rear side 204, the first front side 116, the first bottom side 120, and the first top side 118. The lower portion 106 depicts the second rear side 206, the second front side 112, the second bottom side 108, and the second top side 114. The sealant 104 and the junction 122 are also depicted in FIG. 2.

The upper portion 102 depicts a region on the first top surface 118 that is depressed. This depressed region is where the upper dental arch 438 of the upper jaw 418 of FIG. 4 of FIG. 4 of the user 410 in FIG. 4 will be located. There is a similar region for the lower portion 106 where the second bottom surface 108 is hollow to allow for the lower dental arch 440 to fit into the lower portion. For example, the lower portion covers the lower dental arch 440.

FIG. 2 depicts region 202. Region 202 is the location where the tongue 414 of FIG. 4 can be located. The tongue 414 of FIG. 4 can push against the first rear side 204, and the second rear side 206 thereby further holding in place the oral appliance 110, and blocking air from going through the mouth. The tongue 414 of FIG. 4 can relax and rest against the oral appliance 110, and can be located in region 202.

The lips 406 of FIG. 4 of user 410 of FIG. 4 may be relaxed and partially open, fully opened, partially closed, or closed. However, the amount of air going through the mouth region 434 of FIG. 4 of user 401 of FIG. 4 is controlled by the oral appliance 110. For example, if the oral appliance 110 is configured not to permit air through, then all the air can be directed through the nose and air cannot exit through the mouth region 434 of FIG. 4. A positive air pressure can be generated in an oral cavity 418 of FIG. 4 of the user 410. The tongue 414 of FIG. 4 can naturally aid to hold the oral appliance 110 in place in the mouth region 434 of FIG. 4.

Figure 3:
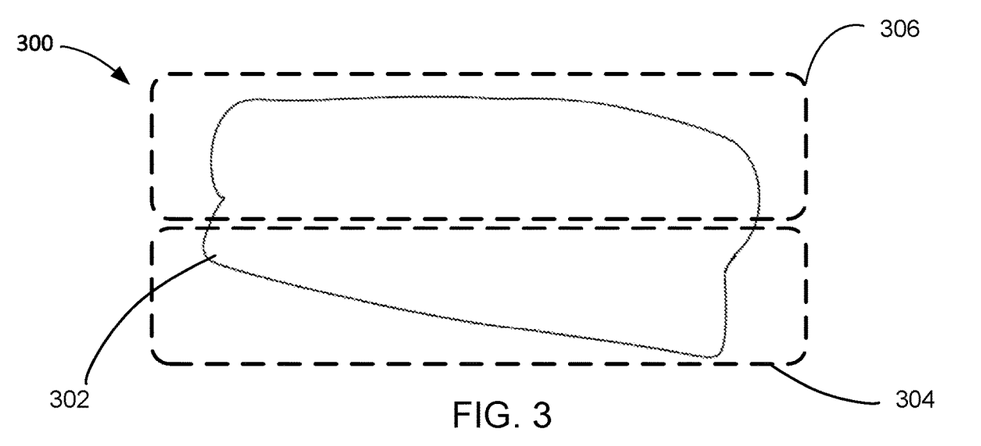
FIG. 3 is another example of an illustration of the front of an embodiment 300 of the present invention.

Referring now to FIG. 3, therein is shown another example of an illustration of the front of an embodiment 300 of the present invention. The one-piece appliance 302 is configured to fit the upper dental arch 438 in FIG. 4 and the lower dental arch 440 in FIG. 4 of the user 410. The upper region 306 depicts the region where the upper dental arch 438 of FIG. 4 will fit into in the one-piece appliance 302. The lower region 304 depicts the region where the lower dental arch 440 of FIG. 4 will fit into in the one-piece appliance 302.

The one-piece appliance 302 functions similar to the oral appliance 110. The one-piece appliance 302 prevents air from exiting the mouth region 434 of FIG. 4 by providing a physical barrier at the mouth region 434 of FIG. 4. The one-piece appliance 302 is held in place by the upper dental arch 438 in the upper jaw 418 of FIG. 4 and the lower dental arch 440 of FIG. 4. The tongue 414 in FIG. 4 of the user 410 in FIG. 4 can also function in a similar manner as the tongue 414 in FIG. 4 functions for the oral appliance 110. The tongue 414 of FIG. 4 helps to hold the one-piece appliance 302 in place as well provide an additional barrier which stops air from entering or exiting the mouth region 434 of FIG. 4 and prevents mouth breathing.

For example, prevent mouth breathing can include the one-piece appliance 302, the oral appliance 110, or a combination thereof completely preventing exhale air from escaping through the mouth region 434, inhale air from entering through the mouth region 434 or a combination thereof. In another example, preventing mouth breathing can include the one-piece appliance 302, the oral appliance 110, or a combination thereof acting as a barrier to prevent exhale air from escaping through the mouth region 434, inhale air from entering the mouth region 434 or a combination thereof.

The one-piece appliance 302 can be constructed from one type of material without the need for any joining of different parts. The one-piece appliance 302 can be made using hypoallergenic and non-toxic material. For example, this can include acrylic, thermoplastic, silicon, rubber, or a combination thereof.

The one-piece appliance 302 can be constructed in various set sizes to generally fit the mouth region 434 of FIG. 4 of the user 410 of FIG. 4. For example, a small size maybe able to fit the user 410 of FIG. 4 who has a small mouth region 434 in FIG. 4. In a further example, if adjustments are needed, a thermoplastic can be used, and a manufacturing process outlined in FIG. 11 can be used to further adjust the one-piece appliance 302 to better fit the mouth region 434 of FIG. 4 for the user 410 of FIG. 4. In a further example, a similar process maybe followed if the user 410 of FIG. 4 requires a medium size, or a large size one-piece appliance 302.

Figure 12:
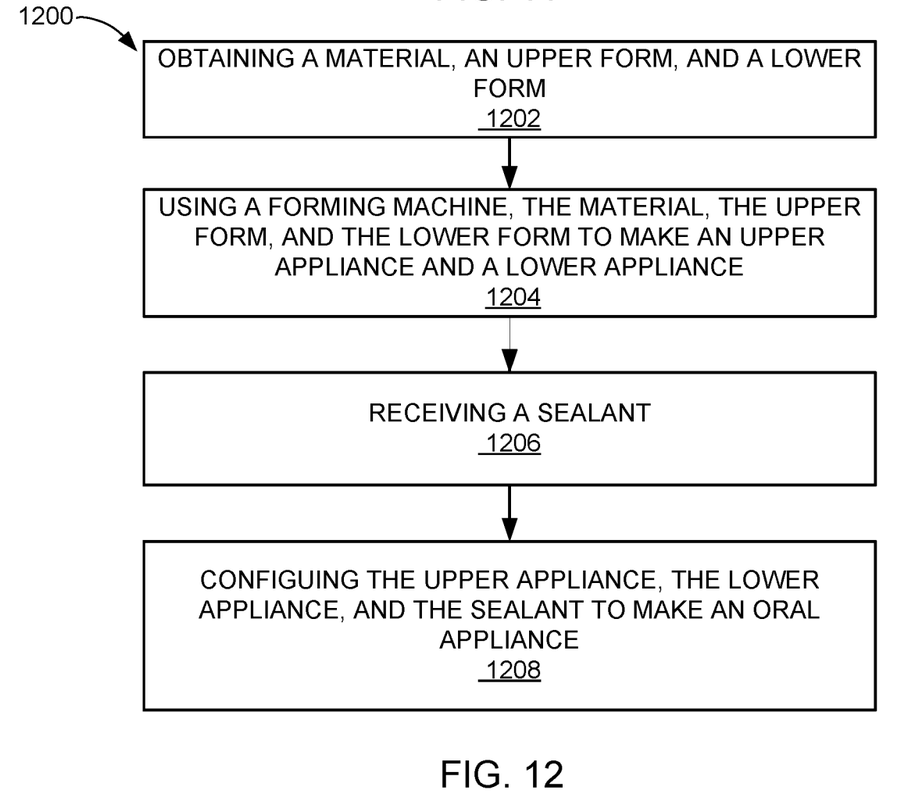
FIG. 12 is another exemplary method of manufacture 1200 of an oral appliance 110, a one-piece appliance 302, or a combination thereof in an embodiment of the present invention

The one-piece appliance 302 can also be constructed to the upper dental arch 438 in FIG. 4 and the lower dental arch 440 in FIG. 4 for user 410 of FIG. 4 in a similar process outlined in FIG. 12. Construction can include molding, or 3-D printing, or a combination thereof.

The upper region 306, and the lower region 304 can be sized to ensure that a complete seal can be formed between the one-piece appliance 302 and the mouth area 434 of FIG. 4 when placed in the appliance location 436 of FIG. 4 of the user 410 of FIG. 4. A third seal can be formed along the upper jaw 418 provided the upper region 306 can cover the upper dental arch 438 of FIG. 4 and the portion of the upper gumline. Similarly, a fourth seal can be formed along the lower jaw 412 provided the lower region 304 can cover the lower dental arch 440 of FIG. 4 and the portion of the lower gumline. The third seal, and the fourth seal together can form a complete seal. The complete seal thereby prevents air from escaping through the mouth.

The upper region 306 dimensions and lower region 304 dimensions can be configured as such to; mold to the upper dental arch 438 of FIG. 4 of the user 410 of FIG. 4, and the lower dental arch 440 of FIG. 4 of a user 410 of FIG. 4; ensure a complete seal is formed for the user 410 of FIG. 4, or; a combination thereof.

Referring now to FIG. 4, therein is shown an example of a section detail view of one embodiment 400 of the present disclosure. A user 410 can include, a nose 402, a nasal vestibule 404, lips 406, a floor of the mouth 408, a lower jaw 412, the lower dental arch 440, a tongue 414, a nasal cavity 416, an upper jaw 418, the upper dental arch 438, an oral cavity 422, a pharynx 424, a larynx 426, a trachea 428, an esophagus 432, a mouth area 434, an appliance location 436 where the oral appliance 110, or the one-piece appliance 302 is placed, an inhale airway path 420, an exhale airway path 430, or a combination thereof.

The nose 402 is the part projecting above the mouth area 434 on the face of a user 410, containing the nasal vestibule 404, and the nasal cavity 416. The nose 402 is used for breathing. The nasal vestibule 404, is the part which first makes contact with inhaled air, or is the exit for exhaled air, or a combination thereof. The nasal vestibule 404 filters the incoming air. After entering through the nasal vestibule 404, the air enters the nasal cavity 416. The nasal cavity is where the incoming air is warmed, moistened, and purified.

The mouth area 434 can be where breathing an happen in a user 410 and the mouth area 434 can be another body orifice through which air can enter or exit into the respiratory tract. The mouth area 434 can include the lips 406, a floor of the mouth 408, a lower jaw 412, the lower dental arch 440, a tongue 414, an upper jaw 418, an oral cavity 422, and an appliance location 436 where the oral appliance 110, or the one-piece appliance 302 can be placed.

The lips 406 act as an opening or closing to the general mouth area 434. The floor of the mouth 408 is the area inside the user just past the lips and over which the tongue 414 can be located. The tongue 414 can be a muscular organ in the mouth area 434 of a user 410, and can be used for impeding airflow through the oral cavity 422.

The oral cavity 422 is the space of the mouth area 434 that includes the lips 406, the lining inside the cheeks and lips, the upper gums, the lower gums the floor of the mouth under the tongue 408, the bony roof of the mouth area 434, and the small area behind the wisdom teeth. Air can be located in the oral cavity 422.

The upper jaw 418 includes the upper dental arch 438 of the mouth area 434, and can be partially covered by an upper gum, and having an upper gumline. The gums are part of the soft tissue lining of the mouth. They surround the teeth and provide a seal around them. The gumline is the line separating the gum from the exposed part of the tooth. The upper dental arch 438 can include the maxillary bone that supports the upper teeth as well as the upper teeth on the maxillary bone itself. The upper dental arch 438 is used to hold the upper portion 102 of the oral appliance 110 in place in an embodiment 100. In another embodiment 300, the upper dental arch is used to hold the upper region 306 of the one-piece appliance 302 in place in the mouth region 434 for a user 410.

The lower jaw 412 has the lower dental arch 440 of the mouth area 434, and can be partially covered by a lower gum, and having a lower gumline. The lower dental arch 440 can include the mandibular bone that supports the lower teeth as well as the lower teeth on the mandibular bone itself. The lower dental arch 440 is used to hold the lower portion 106 of the oral appliance 102 in place in an embodiment 100. In another embodiment 300, the upper dental arch is used to hold the lower region 304 of the one-piece appliance 302 in place in the mouth region 434 for a user 410.

The placement of the upper jaw 418 in relation to the lower jaw 412 can be important with respect to breathing habits, and sleeping habits. Occlusion refers to the alignment of teeth and the way that the upper dental arch 438 and the lower dental arch 440 fit together (bite). The upper dental arch 438 should fit slightly over the lower dental arch 440. The placement of the upper dental arch 438 relative to the lower dental arch 440 can prevent the biting of cheeks and lips, and can protect the tongue 414.

Malocclusion can be caused by a difference between the size of the upper jaw 418, and the size of the lower jaw 412. This relative size difference can cause abnormal bite patterns. The shape of the upper jaw 418, and the lower jaw 412 can be a reason for malocclusion. Other causes can include ill-fitting dental fillings, crowns, dental appliances, retainers, or braces, or misalignment of jaw fractures after a severe injury.

There are different categories of malocclusion. Class 1 malocclusion is the most common. The bite is normal, but the upper dental arch 438 slightly overlaps the lower dental arch 440. Class 2 malocclusion, called retrognathism or overbite, occurs when the upper jaw 418 and upper dental arch 438 severely overlap the bottom jaw 412 and lower dental arch 440. Class 3 malocclusion, called prognathism or underbite, occurs when the lower jaw 412 protrudes or juts forward, causing the lower jaw 412 and lower dental arch 440 to overlap the upper jaw 418 and upper dental arch 438.

The oral appliance 110 can be positioned in an appliance location 436 in the mouth area 434 of a user 410 where the upper dental arch 438, and the lower dental arch 440 are located. Similarly, the one-piece appliance 302 can be positioned in an appliance location 436 in the mouth area 434 of a user 410 where the upper dental arch 438, and the lower dental arch 440 are located.

In an example of the appliance location 436, the oral appliance 110 can be placed over the teeth and over the gumline of the upper jaw FIG. 4 also depicts parts of the respiratory tract. These are the pharynx 424, the larynx 426, and the trachea 428. The pharynx 424 has a role in the respiratory process of a user 410 to allow inhaled air entering the nasal cavity 416 to make its way to the respiratory tract, that can include the larynx 426, the trachea 428 or "windpipe" and finally the lungs where respiration takes place.

The larynx 426 is a part of the respiratory system connecting the pharynx 424 to the trachea 428 in the neck. The larynx 426 allows air to pass through while keeping food and drink from blocking the trachea 428.

The trachea 428 (or windpipe) is a wide, hollow tube that connects the larynx 426 to the lungs. The trachea 428 has the function of providing air flow to and from the lungs for respiration. The esophagus 432 is part of the digestive tract and connects the mouth to the stomach.

The process of respiration of the user 410 is depicted through an inhale airway path 420, and an exhale airway path 430. The lungs of a user 410 bring oxygen into the user 410 when breathing in and send carbon dioxide out of the user 410 when breathing out. The process of breathing in is called inhalation. The process of breathing out is called exhalation.

The inhale air path 420 depicts a possible route for bringing air from the outside into the lungs of the user 410. The air travelling along this route can be called inhalation air, or inhale air as examples. The inhale air path 420 shows a route bringing air in through the nose 402, or through the mouth area 434. If air is inhaled through the nose 402, the air can go through the nasal vestibule 404, the nasal cavity 416, the pharynx 424, larynx 426, and the trachea 428 and then into the lungs. This route is depicted as the inhale air path 420.

If the air is inhaled through the mouth area 434, the air can go through the mouth area 434, into the oral cavity 422, and then into the pharynx 424, larynx 426, and the trachea 428 and then into the lungs.

In an example of an embodiment 100 of the oral appliance 110, the oral appliance 110 can prevent the inhalation of air through the mouth area 434. Thus, air can be inhaled only through the nose 402 by the user 410. The oral appliance 110 can be positioned at an appliance location 436 to ensure that no air can be inhaled through the mouth. This is regardless of whether the mouth area 434 is open or closed.

In another example of an embodiment of the oral appliance 110, the oral appliance 110 can limit or provide a barrier preventing the amount of air that can be inhaled through the mouth area 434. Thus, air can be inhaled trough the mouth area 434, through the nose 402, or a combination thereof, by the user 410.

In another example of an embodiment 300 of the one-piece appliance 302, the one-piece appliance 302 can prevent the inhalation of air through the mouth area 434. Thus, air can be inhaled only through the nose 402 by the user 410. The one-piece appliance 302 can be positioned at an appliance location 436 to ensure that no air can be inhaled through the mouth. This is regardless of whether the mouth area 434 can be open or closed.

The exhale air path 430 depicts a possible route for dispelling air from the lungs of the user 410 into the outside environment. The exhale air path 430 shows the route of air leaving the lungs and going through the nose 402, through the mouth area 434 or a combination thereof. The air travelling along this route can be called exhalation air, or exhale air as examples.

If air is exhaled through the nose 402, the air can go from the lungs through the trachea 428, through the larynx 426, through the pharynx 424, through the nasal cavity 416 and exiting the nasal vestibule 404. This route is depicted as the exhale air path 430.

If the air is exhaled through the mouth area 434, the air can go from the lungs through the trachea 428, through the larynx 426, through the pharynx 424, into the oral cavity 422, and through the mouth area 434 and exit the user 410.

In an example of an embodiment 100 of the oral appliance 110, the oral appliance 110 can prevent the exhalation of air through the mouth area 434. Thus, air can be exhaled only through the nose 402 by the user 410. The oral appliance 110 can be positioned at an appliance location 436 to ensure that no air can be inhaled through the mouth. This is regardless of whether the mouth area 434 is open or closed.

In another example of an embodiment of the oral appliance 110, the oral appliance 110 can limit or provide a barrier preventing the amount of air that can be exhaled through the mouth area 434. Thus, air can be exhaled through the mouth area 434, through the nose 402, or a combination thereof, by the user 410.

In another example of an embodiment 100 of the oral appliance 110, the oral appliance 110 can prevent inhalation, exhalation, or a combination thereof through the mouth area 434 and thus a user 410 can inhale, exhale or a combination thereof through the nose 402.

In a further example of an embodiment 300 of the one-piece appliance 302, the one-piece appliance 302 can prevent the exhalation of air through the mouth area 434. Thus, air can be exhaled only through the nose 402 by the user 410. The one-piece appliance 302 can be positioned at an appliance location 436 to ensure that no air can be inhaled through the mouth. This is regardless of whether the mouth area 434 is open or closed.

In another example of an embodiment 300 of the one-piece appliance 302, the one-piece appliance 302 can prevent inhalation, exhalation, or a combination thereof through the mouth area 434 and thus a user 410 can inhale, exhale or a combination thereof through the nose 402.

The tongue 414 can naturally rest behind the oral appliance in the area 202 of FIG. 2. This can help to add another barrier for the air during breathing in the oral cavity 422. Further, it can help keep the oral appliance 110, or the one-piece appliance 302 in place, keep the complete seal, or a combination thereof.

In an example of an embodiment 100 of the oral appliance 110, the oral appliance is designed to not block the airway during slippage or removal while in the mouth area 434 of the user 410.

In an example of an embodiment 300 of the one-piece appliance 302, the one-piece appliance is designed to not block the airway during slippage or removal while in the mouth area 434 of the user 410.

Figure 5:
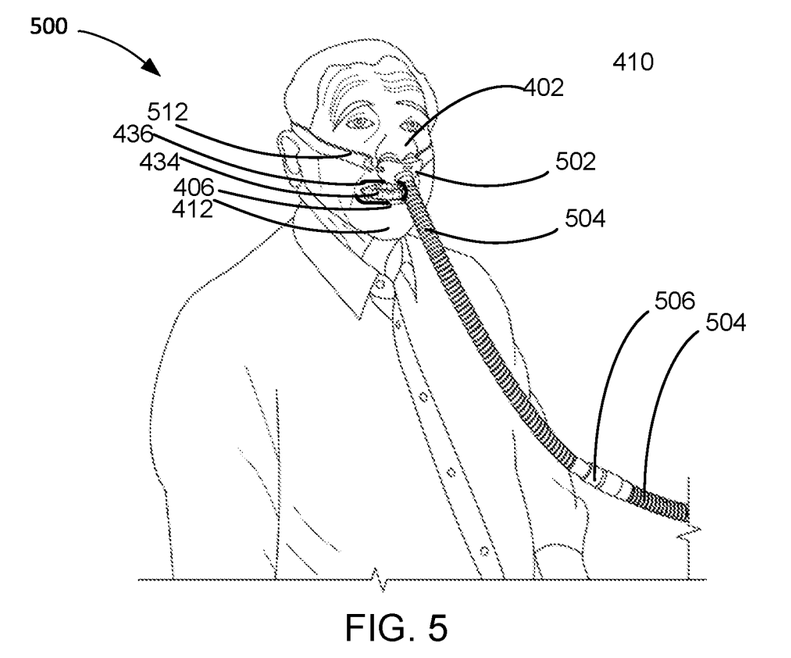
FIG. 5 is an example of a method of use of an oral appliance 110, a one-piece appliance 302, or a combination thereof with a CPAP/BI-PAP system in an embodiment 500 of the present invention.

Referring now to FIG. 5, therein is shown an example of a method of use of an oral appliance 110, a one-piece appliance 302, or a combination thereof with a CPAP/BI-PAP system in an embodiment 500 of the present invention.

Figure 6:
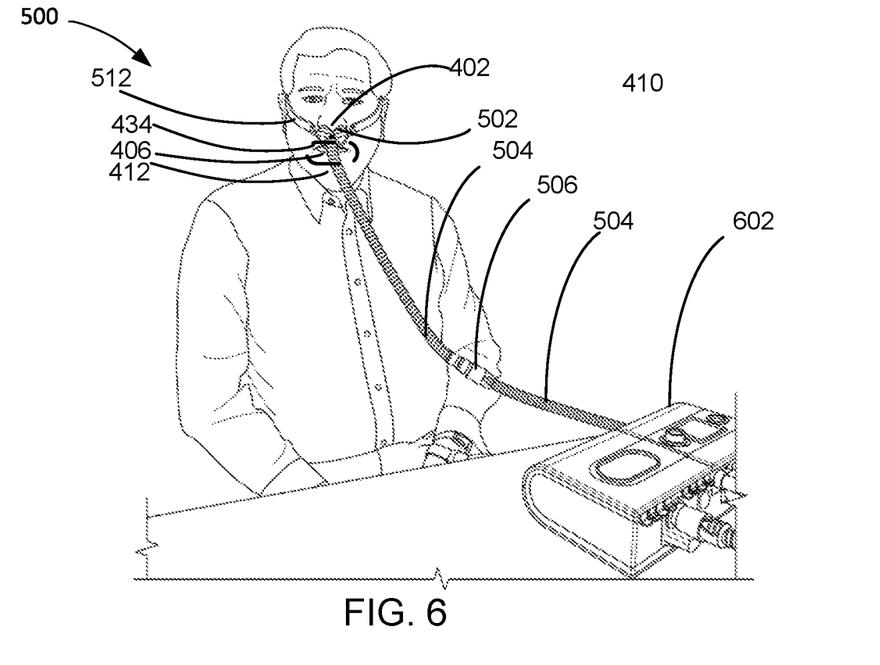
FIG. 6 is another example of a method of use of an oral appliance 110, a one-piece appliance 302, or a combination thereof with a CPAP/BI-PAP system in an embodiment 500 of the present invention.

Also referring now to FIG. 6 is another example of a method of use of an oral appliance 110, a one-piece appliance 302, or a combination thereof with a CPAP/BI-PAP system in an embodiment 500 of the present invention.

FIG. 5 and FIG. 6 both depict the user 410, the nose 402, a nasal mask 502, a hose tube 504, a connector 506, a band 512, the lips 406, the lower jaw 412, and the mouth area 434. FIG. 5. depicts the appliance location 436. FIG. 6 depicts a positive airway pressure (CPAP/BI-PAP) machine 602.

FIG. 5 depicts the band 512. The band 512 is a configuration of a material such as leather, cloth, or other flexible material, often with a fastener, configured to secure or hold onto a mask such as the nasal mask 502, the face mask 702 of FIG. 7.

The nasal mask 502 is triangular in shape and typically covers the area from the bridge of the nose 402 to the upper lip 406. The nasal mask 502 can be used for nose breathing. The nasal mask 502 is connected to the CPAP/BI-PAP machine 602 using the hose tube 504 and the connector 506 when one hose tube 504 is not long enough to connect to the CPAP/BI-PAP machine 602. The CPAP/BI-PAP machine 602, the hose tube 504, and the connector 506, or a combination thereof comprise the positive airway pressure (CPAP/BI-PAP) system 704 of FIG. 7.

FIG. 5 depicts a user 410 using the oral appliance 110 with the nasal mask 502, and the CPAP/BI-PAP machine 602. For example, the user 410 places the oral appliance 110 in the mouth area 434 at the appliance location 436. In this example, the oral appliance 110 is configured to prevent mouth breathing by the user 410. The CPAP/BI-PAP machine 602, the nasal mask 502, the hose tube 504, the connector 506, and the oral appliance 110 are configured to work together so that the user 410 can breathe through the nose only. In this example, the user 410 can include using the oral appliance 110, the nasal mask 502, and the CPAP/BI-PAP system 704 of FIG. 7 to sleep, while being awake, or a combination thereof.

FIG. 6 depicts a user 410 using a one-piece appliance 302, with the mouth area 434 having the lips 506 sealed. The lower jaw 412 does not need to move into any unnatural position. The lower jaw 412, and the upper jaw 418 of FIG. 4 can be in a natural position.

FIG. 6 depicts a CPAP/BI-PAP machine 602. A positive airway pressure machine (CPAP/BI-PAP machine) 602 provides a non-invasive method to deliver pressurized air through a mask to the airways of the user 410. The air pressure keeps the throat muscles from collapsing and reducing obstructions by acting as a splint. There can include two main types of positive airway pressure machines. A Continuous Positive Airway Pressure machine (CPAP), and a Bilevel Positive Airway Pressure machine (BI-PAP also referred to as BPAP). CPAP and BiPAP machines provide a level of positive pressure to the user 410. This can allow the user 410 to breathe easily and regularly, including during a sleeping period. The CPAP/BI-PAP machine 602 is not limited to just a CPAP machine, or a BI-PAP machine. The CPAP/BI-PAP machine 602 can include other similar machines which perform a similar function, to help the user 410 breathe better, through a mask, through the use of forced air pressure, or a combination thereof.

Either a one-piece appliance 302, an oral appliance 110, or a combination thereof can be used with the CPAP/BI-PAP machine 602, the nasal mask 502, the connector 506, and the hose tube 504 for nasal breathing only, partial mouth breathing or a combination thereof.

Figure 7:
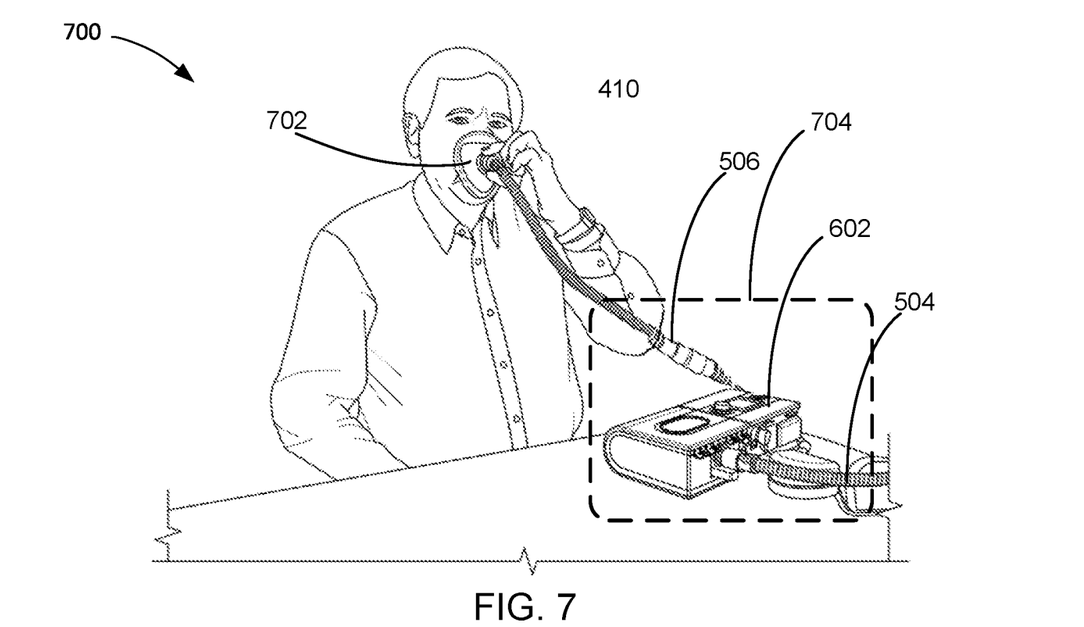
FIG. 7 is a further example of a method of an oral appliance 110, a one-piece appliance 302, or a combination thereof use with a CPAP/BI-PAP system in an embodiment of the present invention.

Referring now to FIG. 7 therein is shown a further example of a method of an oral appliance 110, a one-piece appliance 302, or a combination thereof use with the CPAP/BI-PAP machine 602 in an embodiment of the present invention. FIG. 7 depicts a face mask 702, the CPAP/BI-PAP machine 602, the hose tube 504, and the connector 506. The CPAP/BI-PAP machine 602, the hose tube 504, and the connector 506, or a combination thereof comprise the CPAP/BI-PAP system 704.

The face mask can be used with the one-piece appliance 302, the oral appliance 110, or a combination thereof. Similarly, to the nasal mask 502 in FIG. 5 and FIG. 6, the face mask 702 can be used as a replacement for the nasal mask 502, yet can be used in the same manner as the nasal mask 502 with the one-piece appliance 302, an oral appliance 110, or a combination thereof.

For example, the face mask 702, can be used with the CPAP/BI-PAP system 704, and the one-piece appliance 302, or the oral appliance 110 to prevent mouth breathing for the user 410, and make the user 410 breath through the nose 402 of FIG. 4.

The CPAP/BI-PAP system 704, the CPAP/BI-PAP machine 602, the face mask 702, the oral appliance 110, the one-piece appliance 302, or a combination thereof can be configured to ensure that the user 410 can breathe through the nose 402. In another example the CPAP/BI-PAP system 704, the CPAP/BI-PAP machine 602, the face mask 702, the oral appliance 110, a one-piece appliance 302, or a combination thereof can be configured to ensure that the user 410 can have a barrier to prevent mouth breathing.

For example, the oral appliance 110, the one-piece appliance 302, the CPAP/BI-PAP system 704, the CPAP/BI-PAP machine 602, the face mask 702, or a combination thereof can be configured to provide a barrier to prevent breathing through the mouth area 434 of the user 410. Configuration can include placement of the oral appliance 110, the one-piece appliance 302 into the mouth area 434 to provide a barrier to prevent breathing through the mouth area 434 of the user 410. The lower jaw 412 of FIG. 4 can remain in place without adjustment. For example, an adjustment can include having the lower jaw 412 in an unnatural position for the user 410. In another example, the lower jaw 412 can remain, in a natural position.

Figure 8:
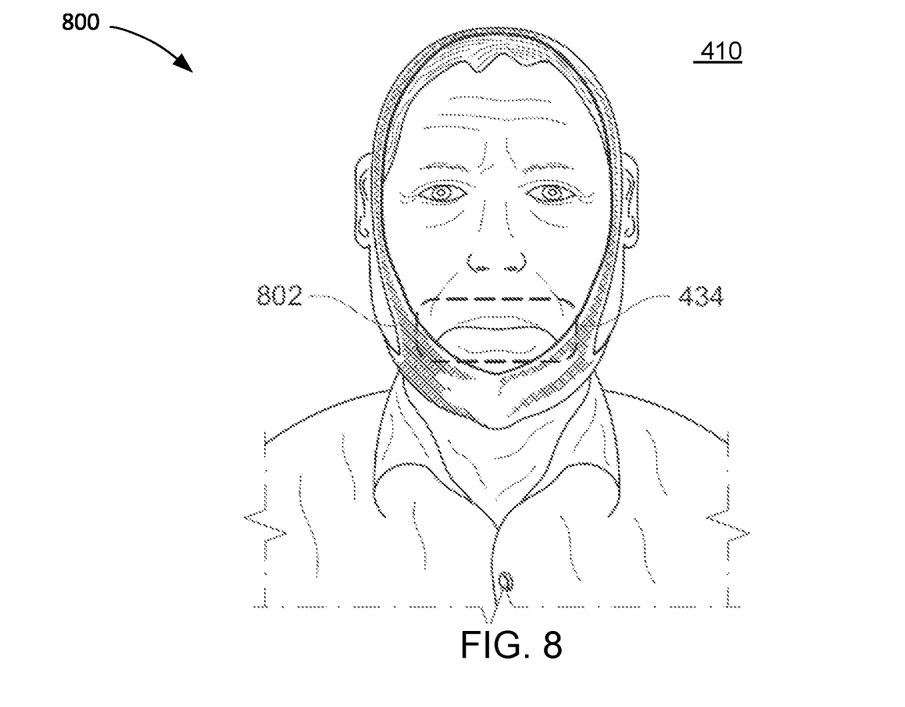
FIG. 8 is another example of a method of an oral appliance 110, a one-piece appliance 302, or a combination thereof use with or without a chin strap in an embodiment of the present invention.

Referring now to FIG. 8, therein is shown an exemplary method 800 of an oral appliance 110, a one-piece appliance 302, or a combination thereof use with a chin strap in an embodiment of the present invention. The method includes the use of a chin strap 802, an oral appliance 110, a one-piece appliance 302 or a combination thereof for only breathing through the nose and preventing breathing through the mouth for a user 410.

FIG. 8 depicts a chin strap 802. The chin strap 802 is constructed of a material such as flexible neoprene, leather, cloth, another flexible material, or a combination thereof, and assists in keeping the lower jaw 412 of FIG. 4 and mouth area 434 of FIG. 4 closed. The chin strap 802, the oral appliance 110, a one-piece appliance 302, or a combination thereof can be configured to ensure that the user 410 can breathe through the nose 402.

For example, the oral appliance 110, the one-piece appliance 302 can be configured to provide a barrier to prevent breathing through the mouth area 434 of the user 410. Configuration can include placement of the oral appliance 110, the one-piece appliance 302 into the mouth area 434 to provide a barrier to prevent breathing through the mouth area 434 of the user 410. The lower jaw 412 of FIG. 4 can remain in place without adjustment. For example, an adjustment can include having the lower jaw 412 in an unnatural position for the user 410. In another example, the lower jaw 412 of the user 410 can remain in a natural position. This can be referred to the lower jaw 412 of the user 410 to sit in a natural position.

In another example, the one-piece appliance 302, or the oral appliance 110, can be configured to operate with a chin strap, a nasal mask, a face mask, the CPAP/BI-PAP system 704, the CPAP/BI-PAP machine 602, or a combination thereof.

Figure 9:
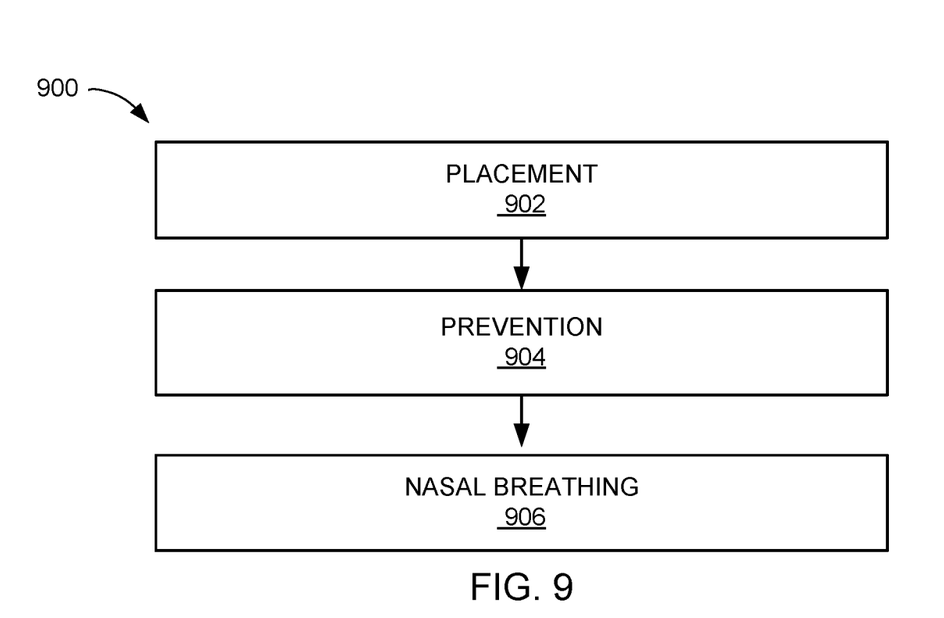
FIG. 9 is an exemplary method 900 of use of an oral appliance 110, a one-piece appliance 302, or a combination thereof in an embodiment of the present invention.

Referring now to FIG. 9, therein is shown an exemplary method 900 of use of an oral appliance 110, a one-piece appliance 302, or a combination thereof in an embodiment of the present invention. The method includes the use of an oral appliance 110, or a one-piece appliance 302 for only breathing through the nose and preventing breathing through the mouth for a user 410 in FIG. 4.

This method 900 includes, a placement step 902 placing the oral appliance 110 or a one-piece appliance 302, in the appliance location 436 of a user 410 in FIG. 4. This can prevent an inhalation breath or an exhalation breath or a combination thereof, from escaping through the mouth of the user 410 in FIG. 4 and can force the air through the nose 402 in FIG. 4 for user 410 in FIG. 4.

For example, the method can assist with a sleep disorder. A sleep disorder can include sleep apnea, snoring, or a combination thereof.

The placement step 902 can include placing the oral appliance 110 or a one-piece appliance 302, in the mouth area 434 of FIG. 4, the appliance location 436 of FIG. 4, or a combination thereof without a need to manipulate the lower jaw 412 in FIG. 4 in order to assist with sleep.

The prevention step 904 can include positioning the oral appliance 110 or a one-piece appliance 302 so that breathing through the mouth by the user 410 of FIG. 4 is obstructed, prevented or a combination thereof.

The nasal breathing step 906 includes that any breathing that occurs can be through the nose 402 of FIG. 4 by the user 410 of FIG. 4.

The method can be used by a user 410 of FIG. 4 when the user 410 is asleep, awake, or a combination thereof to help assist with nasal breathing.

The method does not require adjustment of the lower jaw 412 of FIG. 4 in order to work effectively.

Figure 10:
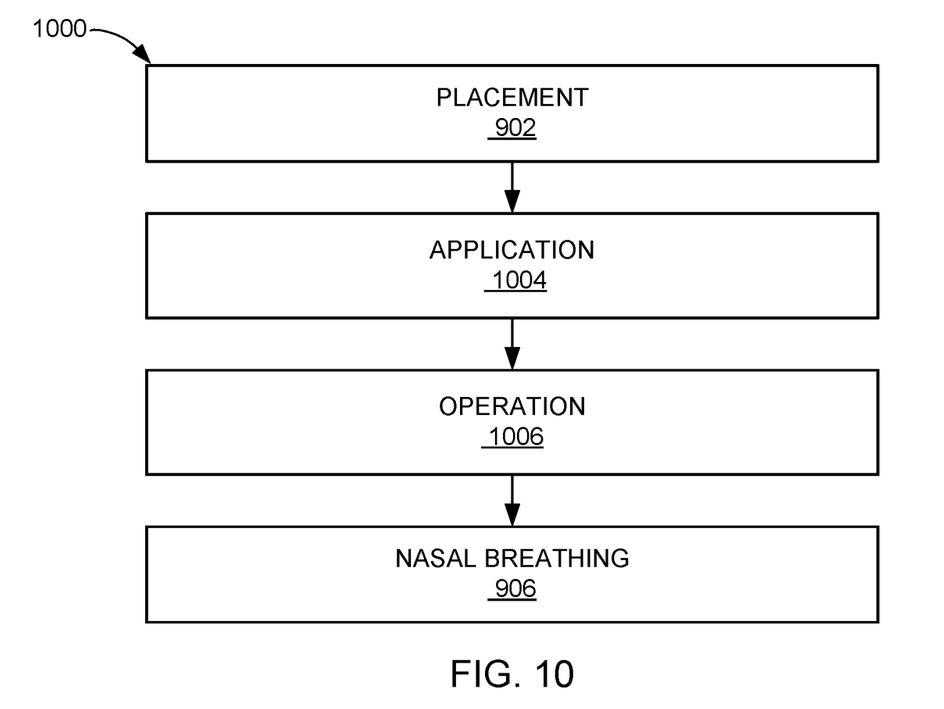
FIG. 10 is an exemplary method 1000 of use of an oral appliance 110, a one-piece appliance 302, or a combination thereof with a CPAP/BI-PAP system in an embodiment of the present invention.

Referring now to FIG. 10, therein is shown an exemplary method 1000 of use of an oral appliance 110, a one-piece appliance 302, or a combination thereof with a CPAP/BI-PAP system in an embodiment of the present invention. The method includes a placement step 902, an application step 1004, an operation step 1006, and the nasal breathing step 906.

The placement step 902 can include placing the oral appliance 110 or a one-piece appliance 302, in an appliance location 436 without a need to manipulate the lower jaw 412 in FIG. 4 in order to assist with sleep.

For example, the method can assist with a sleep disorder. A sleep disorder can include sleep apnea, snoring, or a combination thereof.

The application step 1004 includes placing a mask on the user 410 in FIG. 4. The mask can include a nasal mask 502, a face mask 702, or another type of headgear configured to be used with a CPAP/BI-PAP system 704 of FIG. 7.

The operation step 1006 can include use of the CPAP/BI-PAP system 704 with the oral appliance 110 or a one-piece appliance 302, and the mask such as the nasal mask 502, or face mask 702.

The nasal breathing step 906 includes that any breathing that occurs can be through the nose 402 of FIG. 4 by the user 410 of FIG. 4.

The method can be used by a user 410 of FIG. 4 when the user 410 is asleep, awake, or a combination thereof to help assist with nasal breathing.

The method does not require any adjustment of the lower jaw 412 of FIG. 4 in order to work effectively.

Figure 11:
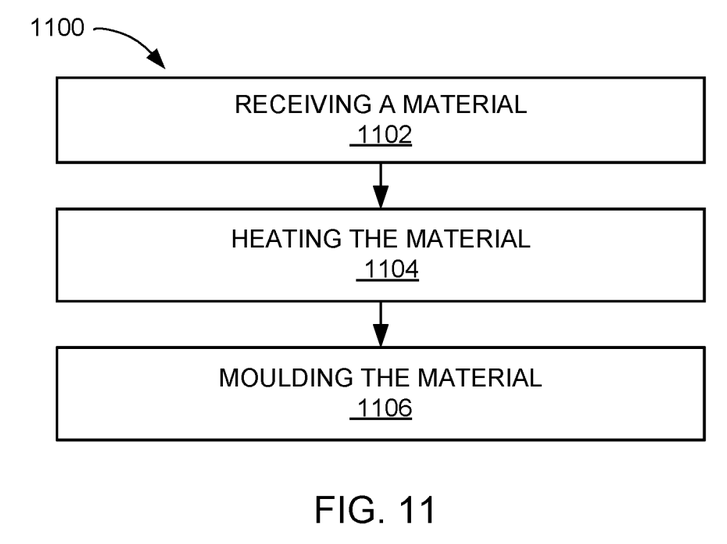
FIG. 11 is an exemplary method of manufacture 1100 of an oral appliance 110, a one-piece appliance 302, or a combination thereof in an embodiment of the present invention.

Referring now to FIG. 11, therein is shown an exemplary method of manufacture 1100 of an oral appliance 110, a one-piece appliance 302, or a combination thereof in an embodiment of the present invention. The method can include receiving a material 1102, heating the material 1104, and molding the material 1106.

The receiving the material 1102 step, and heating the material 1104 step are standard thermal plastic modeling steps. An appropriate material is chosen, and the material is placed in a hot environment. For example, a hot environment may be boiling water. The material becomes soft and is then taken out of the hot environment. This comprises steps 1102, and 1104.

In the molding step 1106, the material is molded. However, the material is molded into a one-piece appliance 302. Generally, appliances and mouth guards are formed in a similar method of manufacture. However, no appliance or mouthguard is formed as a single piece that prevents mouth breathing. This molding step 1106 can include molding the material into an oral appliance 110, or a one-piece appliance 302.

For example, a thermoplastic material prefabricated to a certain size for the user 410 can be placed in boiling water. After 2 minutes the material is removed and after cooling off slightly, the soft material is placed in the mouth of a user 410. The material is soft and casts into the shape of the upper dental arch 438 for the upper region 306, and it can further cast into the shape of the lower dental arch 440 for the lower region 304. After further cooling, the appliance is similar to the one-piece appliance 302.

Referring now to FIG. 12, therein is shown another exemplary method of manufacture 1200 of an oral appliance 110, a one-piece appliance 302, or a combination thereof in an embodiment of the present invention. The method of manufacture can include obtaining a material 1202, forming the material 1204, receiving a sealant 1206, configuring the appliance 1208.

The obtaining material step 1202 can include obtaining a material, an upper form, a and lower form. These are the pieces which can be used to make the oral appliance 110 or the one-piece appliance 302.

Once the materials have been obtained, then a forming machine can be used. An example of a forming machine can include a vacuum forming machine. A form, or a dental impression, is placed with a thermoplastic material in the vacuum forming machine. The material and the form are heated. The heating makings the plastic soft. A vacuum is then applied, and the resulting pressure differential forces the thermoplastic to wrap around the form. After the vacuum is turned off and the material is allowed to cool, the rough material is removed from the vacuum former in the shape of the form. The thermoplastic has been molded. Continuing in this example, an upper appliance 102 of FIG. 1 and a lower appliance 106 of FIG. 1 can be made in this manner.

The next receiving step 1206 includes receiving a sealant 104. The sealant is a material capable of joining the upper portion 102 and the lower portion 106 and can include not to be allergenic or toxic. Thus, the material would have to be non-toxic and hypoallergenic.

The configuration step 1208 includes constructing the oral appliance 102 by adhering the upper portion 102, and the lower portion 106 together as shown and described in FIG. 2. The sealant is used to adhere the upper portion 102 and the lower portion 106. Further the upper portion 102, the lower portion 106 and the sealant 104 are configured to produce an oral appliance 110 that cannot permit breathing through the oral appliance 110 device. In another example, the configuration step 1208 can be used to make a one-piece appliance 302 using a single block of material.

Figure 13:
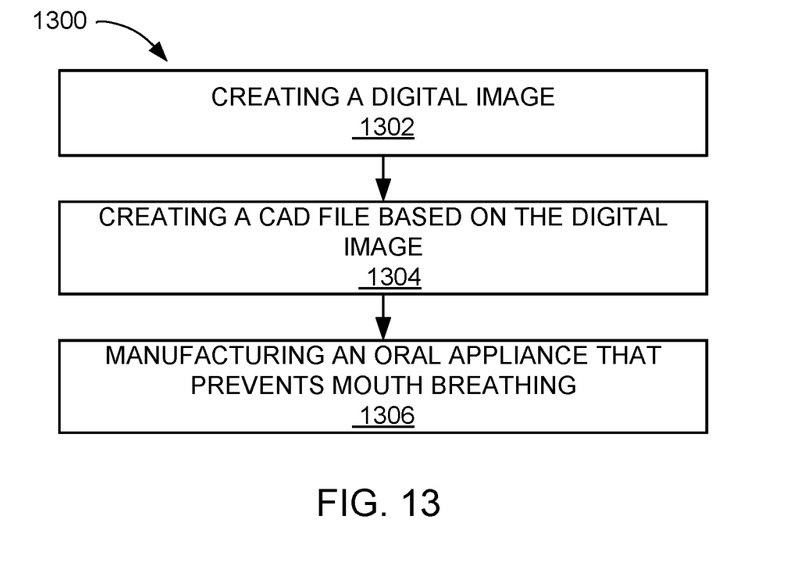
FIG. 13 is further exemplary method of manufacture 1300 of an oral appliance 110, a one-piece appliance 302, or a combination thereof in an embodiment of the present invention.

Referring now to FIG. 13, therein is shown another exemplary method of manufacture 1300 of an oral appliance 110, a one-piece appliance 302, or a combination thereof in an embodiment of the present invention. The method of manufacture uses a three-dimensional (3D) printing methodology. This method of manufacture 1300 can include creating a digital image 1302, creating a computer aided drawing (CAD) file based on the digital image 1304, and manufacturing an oral appliance that prevents mouth breathing 1306.

The creation of a digital image 1302 can include taking an image of a person's mouth area 434 of FIG. 4, appliance location 436 of FIG. 4, or a combination thereof. The location of the image can depend on the appliance location 436 in relation to the mouth area 434. For example, a digital image can be a picture, a digital picture, a digital scan, a model or a combination thereof.

The digital image can be modified enhanced, or a combination thereof as needed so it can be converted into a CAD file. The CAD file can be used by the 3D printer along with a manufacturing technique to create an oral appliance 110, a one-piece appliance 302, or a combination thereof.

The manufacturing an oral appliance that prevents mouth breathing 1306 can include a number of different manufacturing techniques. For example, molding, additive manufacturing, other standardized 3D printing techniques, or a combination thereof can be used to create an oral appliance 110, a one-piece appliance 302, or a combination thereof.

The resulting method, process, apparatus, device, product, and/or system is straightforward, cost-effective, uncomplicated, highly versatile, accurate, sensitive, and effective, and can be implemented by adapting known components for ready, efficient, and economical manufacturing, application, and utilization. Another important aspect of an embodiment of the present invention is that it valuably supports and services the historical trend of reducing costs, simplifying systems, and increasing performance.

These and other valuable aspects of an embodiment of the present invention consequently further the state of the technology to at least the next level.

While the invention has been described in conjunction with a specific best mode, it is to be understood that many alternatives, modifications, and variations will be apparent to those skilled in the art in light of the foregoing description. Accordingly, it is intended to embrace all such alternatives, modifications, and variations that fall within the scope of the included claims. All matters set forth herein or shown in the accompanying drawings are to be interpreted in an illustrative and non-limiting sense.

What is claimed is:

1. An oral appliance device comprising: an oral appliance configured to: fit between a lower jaw and an upper jaw of a user, the oral appliance comprising:
   an upper portion constructed to fit an upper dental arch of the user, and a lower portion constructed to fit a lower dental arch of the user; wherein a first bottom surface of the upper portion is joined to a second top surface of the lower portion using a sealant to form a complete seal between the first bottom surface of the upper portion, and the second top surface of the lower portion;
   wherein the sealant is configured to fill in any gaps along the first bottom surface of the upper portion, and the second top surface of the lower portion;
   wherein the sealant helps to prevent airflow through the oral appliance;
   wherein the oral appliance is configured to prevent airflow from occurring from a mouth area of the user when in use;
   wherein the oral appliance is configured to allow the lower jaw to remain in a natural position;
   wherein a tongue naturally rests against the oral appliance;
   wherein the tongue can hold the oral appliance in place;
   wherein the tongue blocks air from going through the mouth area;
   wherein the tongue helps to keep the complete seal;
   and wherein the mouth area of the user can remain closed.

2. The oral appliance of claim 1 further comprising: wherein the sealant, the upper portion, and the lower portion are constructed of a non-toxic material, a hypoallergenic material or a combination thereof.

3. The oral appliance of claim 1, wherein the oral appliance is configured to operate with a chin strap.

4. The oral appliance of claim 1, wherein the oral appliance is configured to operate with a nasal mask.

5. The oral appliance of claim 1 wherein the oral appliance is configured to operate with a face mask.

6. The oral appliance of claim 1 wherein the oral appliance is configured to operate with a positive airway pressure system.

7. The oral appliance of claim 1 wherein the oral appliance of claim 1 is used to treat a sleep disorder.

8. A one-piece appliance comprising:
   an upper region constructed to fit an upper dental arch of a user, and a lower region constructed to fit a lower dental arch of the user; with the one-piece appliance constructed to fit into an appliance location of the user wherein the one-piece appliance provides a physical barrier to prevent mouth breathing by the user when in use, and wherein the one-piece appliance is configured to allow a lower jaw of the user to remain in a natural position;

wherein a tongue naturally rests against the one-piece appliance;

wherein the tongue can hold the one-piece appliance in place;

wherein the tongue blocks air from going through the mouth;

wherein the tongue helps to keep a complete seal;

and wherein a mouth area of the user can remain closed.

9. The one-piece appliance of claim 8 further comprising: wherein one-piece appliance is constructed of a non-toxic material, a hypoallergenic material or a combination thereof.

10. The one-piece appliance of claim 8 wherein the one-piece appliance is configured to operate with a chin strap, a nasal mask, a face mask, or a combination thereof.

11. The one-piece appliance of claim 8 wherein the one-piece appliance is configured to operate with a positive airway pressure system.

12. The oral appliance of claim 8 wherein the oral appliance of claim 8 is used to treat a sleep disorder.

13. A method of treating a sleep disorder comprising: placing an oral appliance, a one-piece appliance, or a combination thereof in an appliance location of a user; preventing breathing through a mouth area of the user using the oral appliance, the one-piece appliance, or a combination thereof; wherein the oral appliance, the one-piece appliance, or a combination thereof is configured to allow a lower jaw of the user to remain in a natural position; wherein a tongue naturally rests against the oral appliance, the one-piece appliance, or a combination thereof; wherein the tongue can hold the oral appliance, the one-piece appliance, or a combination thereof in place; wherein the tongue blocks air from going through the mouth area; wherein the tongue helps to keep a complete seal; and wherein the mouth area of the user can remain closed.

14. The method of claim 13 further comprising: using a positive airway pressure system by the user.

15. The method of claim 13 where the sleep disorder can be sleep apnea.

16. The method of claim 13 wherein the sleep disorder can be snoring.

* * * * *